(12) United States Patent
Frappier et al.

(10) Patent No.: US 6,403,825 B1
(45) Date of Patent: Jun. 11, 2002

(54) PROCESSES FOR PRODUCING CITRATE ESTERS

(75) Inventors: Edward P. Frappier, Kernersville; James E. Davis, Greensboro, both of NC (US); Martin Grendze, Indianapolis, IN (US); Eric F. V. Scriven, Greenwood, IN (US); John T. Wyeth, Indianapolis, IN (US); Kuen-Wai Chiu, Greensboro, NC (US)

(73) Assignee: Reilly Industries, Inc., Indianapolis, IN (US)

( * ) Notice: Subject to any disclaimer, the term of this patent is extended or adjusted under 35 U.S.C. 154(b) by 0 days.

(21) Appl. No.: 09/437,334

(22) Filed: Nov. 30, 1999

Related U.S. Application Data

(63) Continuation of application No. PCT/US98/09635, filed on May 12, 1998.
(60) Provisional application No. 60/046,251, filed on May 12, 1997.

(51) Int. Cl.$^7$ .............................................. C07C 69/66
(52) U.S. Cl. ........................ 560/180; 560/176; 560/185
(58) Field of Search ................................ 560/176, 180, 560/185

(56) References Cited

U.S. PATENT DOCUMENTS

| | | | |
|---|---|---|---|
| 3,438,863 A | 4/1969 | Batti ............................ | 195/36 |
| 3,632,476 A | 1/1972 | Fried ........................... | 195/37 |
| 3,950,397 A | 4/1976 | Batelaan .................. | 260/484 P |
| 4,155,811 A | 5/1979 | Nubel et al. .............. | 195/28 R |
| 4,278,764 A | 7/1981 | Rottigni et al. ............. | 435/144 |
| 4,324,906 A | 4/1982 | Gutierrez et al. ........... | 560/176 |
| 4,711,922 A | 12/1987 | Hull et al. ................... | 524/310 |
| 4,714,767 A | 12/1987 | Tanaka et al. .............. | 548/344 |
| 4,789,700 A | 12/1988 | Hull et al. ................... | 524/310 |
| 4,824,893 A | 4/1989 | Hull ............................ | 524/310 |
| 4,870,204 A | 9/1989 | Hull et al. ................... | 560/180 |
| 4,892,967 A | 1/1990 | Hull et al. ................... | 560/180 |
| 4,931,583 A | 6/1990 | Hull et al. ................... | 560/180 |
| 4,972,036 A | 11/1990 | Elmore et al. .............. | 526/210 |
| 5,055,609 A | 10/1991 | Hull et al. ................... | 560/180 |
| 5,081,025 A | 1/1992 | Kirkovits et al. ........... | 435/144 |
| 5,210,296 A | 5/1993 | Cockrem et al. ........... | 562/589 |
| 5,227,155 A | 7/1993 | Castrogiovanni et al. ..... | 424/61 |
| 5,237,098 A | 8/1993 | Bemish et al. .............. | 562/584 |

FOREIGN PATENT DOCUMENTS

| | | |
|---|---|---|
| CS | 155485 | 10/1974 |
| DE | 1041944 | 10/1958 |
| DE | 4242622 | 6/1994 |
| JP | 48004554 | 2/1973 |
| WO | WO 97/30964 | 8/1997 |

OTHER PUBLICATIONS

Purification of Laboratory chemicals, Perrin et al, 1986, pp. 38–39.*
Abstract; M. Chen, M. Yang, F. Zhang, B. Li, "Esterification Catalyzed By Stannous Oxide", *Youji Huaxue* (1990), 10(1), 86–9.
Abstract; D.J. Gilbert, B.D. Silverstein, "Synthesis Of Triethyl Citrate", *Chemistry* (1968), 41(6), 29–32.
Abstract; O.E. Krivoshchekova, A.A. Shamshurin, V.A. Antonova, "Esterification Of Dicarboxylic And Some Other Acids By Pyrocarbonic Esters", *Izv. Akad. Nauk Mold. SSR, Ser. Biol. Khim. Nauki* (1967), No. 10, 63–6.
Abstract; S. Peng, C. Feng, W. Shu, "Synthesis Of Tributyl Citrate With Solid Acid Catalyst", *Xiandai Huagong* (1995), 15(12), 30–1.
Abstract; I. Perl Molnar, M. Szakacs Pinter, V. Vonsik Fabian, "Esterification Of Carboxylic Acids With Butanol In Aqueous Solutions For Their Gas Chromatographic Analysis", *Magy. Kem. Foly.* (1985), 91(10), 459–73.
Abstract; D.J. Raber, P. Gariano, Jr., A.O. Brod, A. Gariano, W.C. Guida, A.R. Guida, M.D. Herbst, "Esterification Of Carboxylic Acids With Trialkyloxonium Salts", *J. Org. Chem.* (1979), 44(7), 1149–54.

* cited by examiner

Primary Examiner—Samuel Barts
(74) *Attorney, Agent, or Firm*—Woodard, Emhardt, Naughton Moriarty & McNett

(57) ABSTRACT

Described are processes for producing citrate esters in, an economic fashion. Esters are prepared by esterification of a citric acid-containing fermentation broth having been treated to remove cations and optionally other impurities, but containing sugar(s). Esters are also prepared by reacting an impure aqueous citric acid source with an alcohol to provide a heterogeneous aqueous/organic reacted mixture, wherein the organic phase contains the ester and the aqueous phase retains water-soluble impurities. A liquid phase separation is then used to separate the organic and aqueous phases, conveniently separating the impurities from the product and avoiding the energy-intensive distillation of water from the reaction medium.

20 Claims, 1 Drawing Sheet

PROCESSES FOR PRODUCING CITRATE ESTERS

This application is a continuation of PCT/US98/09635 filed May 12, 1998 which claims benefit of Provisional No. 60/046,251 filed May 12, 1997.

BACKGROUND

This invention relates generally to processes for producing citrate esters, and more particularly to processes useful for preparing citrate esters from partially purified citric acid-containing fermentation broths.

As further background, citric acid is a biologically occurring material which finds use in the food, pharmaceutical, cosmetics and plastics industries. In the plastics industry in particular, citric acid serves as a raw material for the manufacture of citrate ester plasticizers.

Since the early work of C. Wehmer beginning in the 1890's, there has been substantial interest and investment in fermentation processes for producing citric acid. As such, nearly all of the 700 million pounds or more of citric acid produced worldwide yearly are from fermentation processes, for instance by the fermentation of a carbon source such as molasses with the microorganism, Aspergillus Niger. Typically, broths from such fermentations will contain about 10 weight % or more citric acid, as well as about 1000 ppm or more salts, about 1 weight % carbohydrates, and 2 weight % proteins, amino acids and other materials.

Purification of citric acid from such mediums has itself been the subject of substantial attention in the academia and industry. In general, three techniques have been used to date, those being precipitation, solvent extraction and solid-phase polymer adsorption and subsequent desorption. As to the first technique, precipitation, it can be fairly stated that it has been the more preferred technique used on a commercial scale, even though significant endeavors as to the other two techniques have been made. In precipitation, calcium hydroxide (lime) is usually added to the fermented medium to form the slightly soluble tricalcium citrate tetrahydrate. Properly performed, this precipitation leaves most impurities in the solution. Impurities may further be removed by washing the filtered precipitate. To further purify the product, the moist precipitate is reacted with sulfuric acid to yield calcium sulfate (gypsum) and a solution of free acid. The free acid solution is then treated with activated carbon and ion exchange resins before evaporation to the crystalline citric acid product. As is recognized, the efficacy of this precipitation method is highly dependent on properly and carefully performing the various steps involved. It is thus a sensitive process requiring high refinement, especially on a commercial scale.

A second technique which has been used to purify citric acid is solvent extraction. In this technique, citric acid is extracted from the fermentation broth with solvent hydrocarbons, for example, octane, benzene, kerosene, ethers, esters, ketones or amines. Citric acid is then reextracted from the solvent phase into water with either the addition of heat or the formation of a citric acid salt. However, this solvent extraction technique is also expensive and complex. Further, solvent extraction generates a very substantial amount of waste for disposal, which from both cost and environmental standpoints is unattractive.

A third technique which has been suggested involves the use of solid adsorbents to remove citric acid from the medium. The adsorbed citric acid is then recovered from the polymer utilizing a desorbing agent. For example, U.S. Pat. No. 4,323,702 to Kawabata et al. describes a process for recovering carboxylic acids with a material of which the main component is a polymeric compound having a pyridine skeletal structure and a cross-linked structure. The captured carboxylic acids are then desorbed using an aliphatic alcohol, an aliphatic ketone or a carboxylic ester as the desorbing agent. U.S. Pat. No. 4,720,579 to Kulprathipanja describes a process in which citric acid is separated from a fermentation broth using an adsorbent of a neutral, noniogenic, macroreticular, water-insoluble cross-linked styrene-poly(vinyl)benzene, and desorbed with an acetone/water mixture.

In U.S. Pat. No. 4,851,573 to Kulprathipanja et al., another process is described in which an adsorbent of a cross-linked acrylic or styrene resin matrix having attached tertiary amine functional groups or pyridine functional groups is used as an adsorbent for the citric acid, which is desorbed preferably with sulfuric acid. In still another patent, U.S. Pat. No. 4,851,574, Kulprathipanja describes separating citric acid from a fermentation broth using an adsorbent of a cross-linked acrylic or styrene resin matrix having attached aliphatic quaternary amine functional groups.

As will be appreciated, the above-described techniques for purifying citric acid, as well as final crystallization processes generally used in all of them to remove sugars, add significant cost to the final product. In turn, significant costs are added to products downstream of citric acid. For example, as previously indicated, among its other uses, citric acid is an important starting material to citrate esters which have been found to be particularly useful as plasticizers for PVC compositions, see, e.g. U.S. Pat. Nos. 4,870,204; 4,789,700; 4,711,922; and 4,824,893; and biodegradable polymer compositions, see, e.g., U.S. Pat. No. 5,556,905. For the most part, citrate esters have been prepared by esterification of purified citric acid, e.g. technical or USP grade, with the appropriate alcohol and in the presence of an esterification catalyst. However, the cost pressures caused by using such purified grades of citric acid are a significant disadvantage, as the citrate esters are made and used in relatively large quantities.

German Pat. No. 1 041 944 describes a process in which a citric acid ester is said to be prepared from a crude citric acid broth. Specifically, the authors describe a process for producing an ester of citric acid, in which a raw 30% citric acid broth is dehydrated with benzene and ethanol to a syrup. Butanol and butyl acetate, along with a tin catalyst, are added to the syrup and the mixture is heated to a temperature of 140–160° C., whereupon the reaction is halted with potassium hydroxide. The resulting reaction product is washed with sodium carbonate in water, and the crude mixture distilled. The authors report yielding acetyl tributyl citrate in the recovered material.

In light of the above, there remains a need for economic routes to important citrate esters useful as plasticizers. Desirably, such routes would avoid the high costs of purification while yielding citrate ester products suitable for use as industrial plasticizers for PVC and other plastics. The present invention is addressed to these needs.

SUMMARY OF THE INVENTION

One feature of the present invention is the surprising discovery that desirable citrate ester products can be prepared by esterification of relatively impure citric acid-containing fermentation broths, if such broths are treated to remove cations prior to the esterification. Accordingly, one preferred embodiment of the present invention provides a process for preparing a citrate ester which includes (i) providing a citric acid-containing broth from a citric acid-producing fermentation, the broth having been treated to remove cationic impurities; and (ii) reacting the citric acid-containing broth with an alcohol to esterify the citric acid and form a citrate ester. It has been found that the removal of the cations prior to conducting the esterification minimizes the formation of particulate impurities otherwise produced, and significantly improves the reaction rate and the product yield and product purity. This surprising aspect of the invention provides for an economic production of citrate esters while avoiding the costs associated with bringing the citric acid to a purified state such as a technical or USP grade citric acid.

In a particularly preferred aspect, the invention provides processes as described above for preparing a citrate triester composition of Formula I:

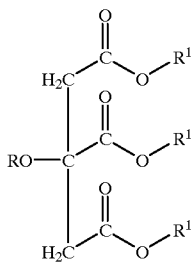

wherein

R=H, $R^2$—CO— or Ph(—$R^2$)$_n$—CO— wherein $R^2$ is a $C_1$ to $C_{18}$ aliphatic group, n is 0 or 1, and Ph is a phenyl group;

each $R^1$, which can be the same or different from each other, is selected from H, a $C_1$ to $C_{18}$ aliphatic group or alicyclic group, or $R^2$ (O$R^3$)$_m$— wherein $R^2$ is as defined above, $R^3$ is a $C_1$ to C8 alkyl group, and m is an integer from 1 to 15; and wherein up to about 40% of the groups $R^1$, taken together, are H (i.e. the carboxylic acid groups in the ester compositions are about 60% to about 100% esterified). This process of the invention includes (i) reacting a citric acid-containing fermentation broth having been treated to remove cations, with one or more alcohols of the formula $R^1$—OH wherein $R^1$ is as defined above, to form a citrate ester of Formula I wherein R=H, and (ii) optionally reacting the product of step (i) with an acid halide or anhydride of the formula $R^2$CO—X, Ph(—$R^2$)$_n$—CO—X, $R^2$—CO—O—CO—$R^2$, or Ph(—$R^2$)$_n$—CO—O—CO—(—$R^2$)$_n$—Ph wherein $R^2$ and n are as defined above and X is a halogen, to form a product of Formula I wherein R=$R^2$—CO— or Ph(—$R^2$)$_n$—CO— wherein $R^2$, n and Ph are as defined above.

Another preferred embodiment of the present invention provides a process for preparing a citrate ester which includes (i) combining an alcohol and an aqueous citric acid source containing water-soluble impurities to provide a reaction medium having an aqueous phase; (ii) reacting the reaction medium form a citrate ester, said citrate ester passing to an organic phase separate from said aqueous phase, said aqueous phase substantially retaining said water-soluble impurities; and (iii) separating the organic phase, containing the citrate ester, from the aqueous phase. In one form, this embodiment is applied to the formation of citrate esters which themselves are sufficiently insoluble in water to form a separate organic phase. In other forms, this embodiment is applied to the formation of citrate esters which are relatively soluble in water, and an inert, water-insoluble organic solvent is added to the reaction medium to provide the organic phase, into which at least a portion of the citrate ester product passes and is thereby separated from the water-soluble impurities remaining in the aqueous phase. In either form, the removal of the citrate ester product from the reacting aqueous phase drives the equilibrium of the esterification toward the ester product, thereby benefiting the preparative process. Advantageously, when using an unpurified or partially-purified citric acid fermentation broth as the citric acid source in such processes, water-soluble impurities such as salts, sugars, and/or other water-soluble organic compounds, are readily separated from the citrate ester product. Preferred citrate esters in this embodiment of the invention are those of Formula I. Thus, as discussed above, an acid halide or anhydride can be reacted with the resulting citrate ester product to functionalize its hydroxyl group.

A particularly preferred embodiment of the invention provides a process for preparing tributyl citrate. The process comprises reacting butanol (preferably n-butanol) with aqueous citric acid to form tributyl citrate, the reacting being conducted under conditions sufficient to provide a reacted medium including an aqueous phase and a separate organic phase containing the tributyl citrate. The organic phase is then separated from the aqueous phase to recover the tributyl citrate.

Additional preferred embodiments of the present invention provide citrate ester compositions produced by the methods described herein, and polymer compositions physically modified, e.g. plasticized, by such citrate ester compositions.

The present invention provides improved processes for economically preparing citrate esters, suitable e.g. for use as plasticizers, as well as citrate esters preparable by such processes and polymer compositions physically modified by such esters. Additional objects, features and advantages of the invention will be apparent from the description which follows.

DESCRIPTION OF THE PREFERRED EMBODIMENTS

Figure 1:
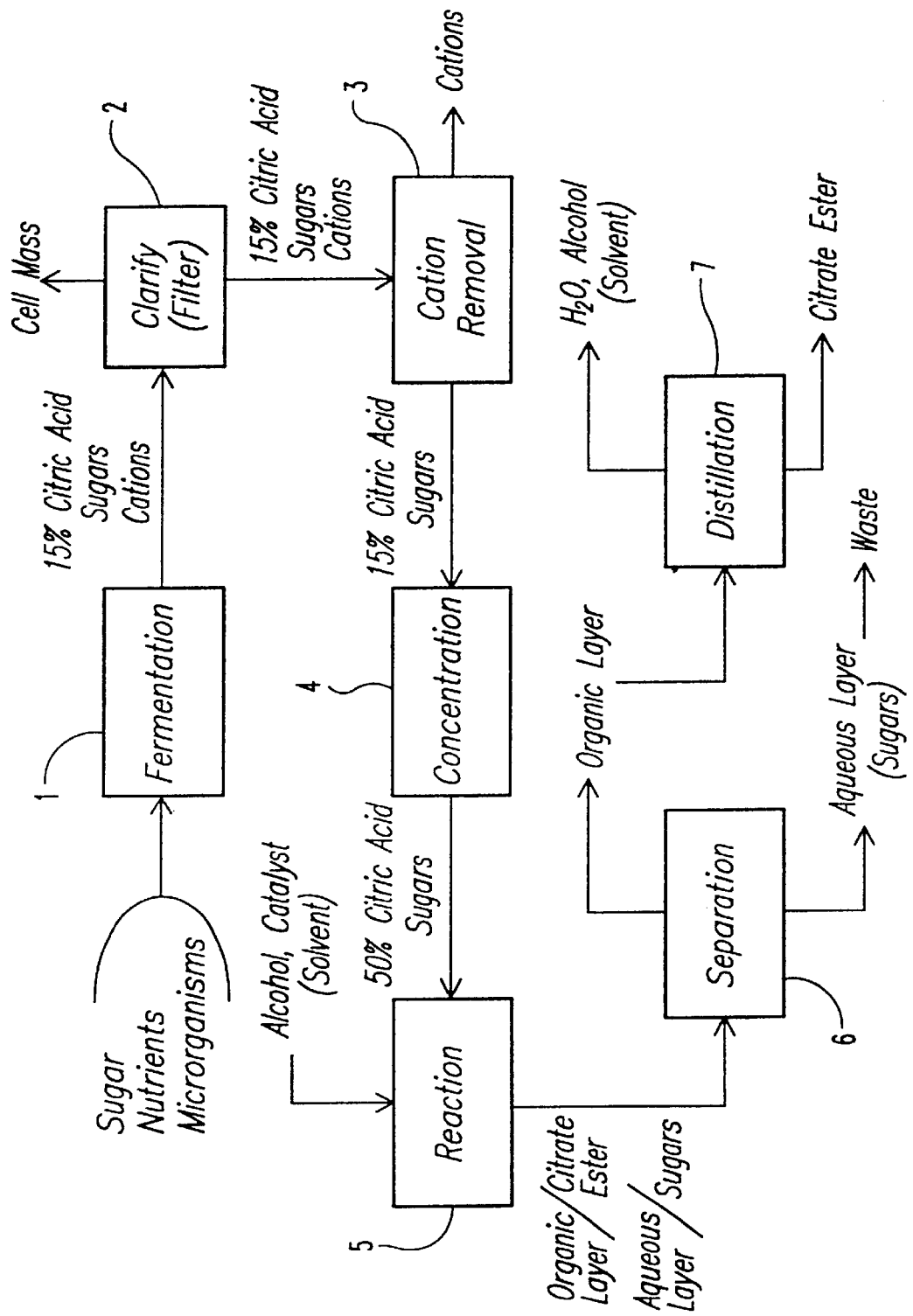
FIG. 1 provides a schematic diagram of a preferred overall process of the invention for producing a citrate ester.

For the purpose of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention relates.

As disclosed above, the present invention features the discovery of improved processes for preparing citrate ester compositions. In accordance with one aspect of the invention, a citric acid-containing fermentation broth, having been treated to remove cations, is reacted with an alcohol to form a citrate ester. It has been discovered that while attempts to directly esterify citric acid fermentation broths (containing substantial cations) yield undesirable particulate-containing crude mixtures, the esterification of a citric acid fermentation broth which has been treated to remove cations yields a relatively advantageous, substantially particulate-free citrate ester product.

In accordance with another aspect of the invention, a citrate ester is prepared by combining an alcohol and an aqueous citric acid source containing water-soluble impurities (e.g. salts, sugars, etc. typically present in a fermentation broth) to provide a reaction medium having an aqueous phase. This reaction medium is reacted to form a citrate ester. The citrate ester passes into an organic phase separate from the aqueous phase, whereas the aqueous phase retains water-soluble impurities. The organic phase containing the citrate ester is then separated from the aqueous phase, for example by a conventional layer separation technique such as decantation or the like.

Turning now to starting materials useful in the present invention, the citric acid source may be a citric acid-containing broth resulting from a citric acid-producing fermentation. For example, the broth may be from a fermentation of a carbon source (e.g. carbohydrates such as corn sugar, molasses or potato extracts) with a suitable citric acid-producing microorganism such as Aspergillus Niger. For additional information as to citric acid fermentations, reference can be made to an abundant body of literature thereon, including for example U.S. Pat. Nos. 3,438,863; 3,632,476; 41155,811; 5,081,025; and 5,237,098.

As will be appreciated by those skilled in the field, citric acid fermentation broths will typically contain water, citric acid, sugars, salts, amino acids, proteins and other various components in minor amounts. Usually, a broth from the fermenter will contain citric acid at a level of about 10 weight % or more, typically 10 weight % to 20 weight %, and the salt concentration will typically be about 1000 ppm or more. Such broths are rendered free of insoluble organic or inorganic matter that occurs in raw broths by conventional clarification methods such as filtration.

For certain preferred processes of the invention, such broths are treated to achieve partial purification, including removal of cations, but are substantially less pure than technical or USP grade citric acid materials and include substantial sugar. Prior to the esterification step of the present invention, the broths can optionally also be concentrated by evaporation or any other suitable means. In this regard, evaporation can be conducted, for example, to concentrate the broth to greater than 30 weight % citric acid, e.g. 30 weight % to 60 weight %, and typically about 50%, prior to the esterification reaction.

As to the removal of cations from the broth, this can be accomplished, for instance, by treating the crude citric acid-containing fermentation broth (after removal of cell mass from the fermented medium) with a suitable cation exchange resin in the acid form. Such treatments can involve passing the broth through a column containing the cation exchange resin, in gel or macroreticular (macroporous) form, and collecting the cation-depleted eluent broth. As to specific cation exchange resins suitable for this purpose, these include Amberlyst 15, Amberlite 120, Amberlite 200, all commercially available from Rohm & Haas, in addition to a wide variety of other cation exchange resins known to those skilled in the relevant field. As to the cations themselves which are removed, as is known, fermentation broths typically contain a variety of salts, including K, Na, Ca, Mg and Fe cations. These will be removed effectively to prevent the formation of undesirable solids in the subsequent esterification, and/or to convert their corresponding anions to acid forms which may assist in catalyzing the esterification reaction.

For use in the invention, the broth may also optionally be treated to remove other materials. For instance, the broth may be treated to substantially remove anions and/or amino acids and/or proteins present as impurities from the fermentation. In accordance with the invention, however, it has been discovered that treatment to render the broth free of sugars, which are difficult to separate from the citric acid, is not necessary to achieving an acceptable citrate ester product, even when the esterification is conducted while distilling off water. Thus, in general, while other impurities may be removed, the broth reacted in the preferred esterification step of the present invention can contain substantial sugar, e.g. at least about 1% sugar by weight, typically in the range of about 1% to about 20% sugar by weight. This sugar may be found in the form of one or more sugars, for example including glucose, sucrose, xylose, mannose, maltose, fructose and/or galactose.

In accordance with one aspect of the invention, the esterification reaction is conducted under distillative conditions, removing water from the reaction mixture in the distillation pot. For reactions utilizing relatively volatile alcohols, e.g. methanol or ethanol, additional amounts of the alcohol can be added during the course of the distillation/reaction. When less volatile alcohols are used, e.g. butyl alcohol or higher chain alcohols, the addition of further amounts of alcohol is generally not necessary. In addition, such distillations can, if desired, be conducted in the presence of an agent which azeotropes with water.

In accordance with another aspect of the invention, the esterification reaction can be conducted under non-distillative conditions. In this aspect, an aqueous, impurity-containing citric acid source can be reacted with an alcohol to prepare a citrate ester product, which product passes into a separate organic phase as it is formed. After the reaction has achieved a desired level of conversion, for example above 50%, preferably above 80%, and more preferably above 90%, the organic phase is separated from the liquid phase. In this fashion, the ester product is recovered in the organic phase and is facilely separated from both the water and water-insoluble impurities, while avoiding the need for distillative separation of the water. As such, substantial energy requirements for water vaporization (e.g. in a distillative esterification) are avoided. In addition, this avoids contamination and/or colorization of the product by water-soluble impurities such as salts, sugars and the like, and/or by thermal decomposition products of such impurities that may occur in a rigorous distillation. After isolation in the organic phase, the citrate ester product can be further purified as necessary.

In the case of citrate esters which are essentially completely or relatively insoluble in water, the citrate ester by itself may form the separate organic phase. In such cases, it is not necessary to include any further agent or inert organic solvent in the reaction medium to provide the organic phase, although one can be included if desired. For example, in the preferred preparation of tri-n-butyl citrate by reacting citric acid with n-butyl alcohol, the initial reaction medium occurs as a single, aqueous phase. The tri-n-butyl citrate product is relatively insoluble in water, and therefore forms a separate organic phase as it is formed.

In the case of citrate esters that are relatively soluble in water, an additional agent such as an inert organic solvent can be included in the reaction medium to provide for a separate organic phase containing the citrate ester product. Suitable inert organic solvents for these purposes include water-insoluble aromatic solvents such as toluene, benzene, xylenes, ethylbenzene, and the like, as well as water-insoluble aliphatic solvents having up to about 20 carbon atoms, e.g. hexanes, octanes, heptanes, decanes, and the like, ethers such as diphenylether, diphenylethane, etc., and halogenated solvents such as chloroform, carbon tetrachloride, chlorobenzene, chlorofluorocarbons, and the like.

Alternatively or in addition to using a water-insoluble organic solvent, a water-soluble separating agent can be added to the reaction mixture that decreases the solubility of the citrate ester product in the aqueous phase, thus causing citrate ester product to form or enter into a separate organic phase. For example, a water-soluble salt, such as an alkali or alkaline earth metal halide, e.g. sodium chloride, calcium chloride, potassium chloride, etc., can be added for these purposes. Processes conducted in accordance with this aspect of the invention are particularly advantageous when employed using a relatively impure citric acid starting material, in that water-soluble impurities such as sugars and salts are separated from the citric acid ester product due to their solubility in the aqueous phase. In a corresponding distillative process, such salts, sugars and/or other impurities would remain in the pot with the citric acid ester product, and potentially contaminate the product. Moreover, the liquid phase separation of the organic and aqueous phases avoids the energy requirements associated with a distillative separation of the water in the reaction medium.

Processes in accordance with this aspect of the invention are preferably conducted with stirring or other agitation. In preferred processes, the reaction mixture forms an emulsion when agitated. In addition, as those skilled in the art will recognize, such processes can be conducted at any suitable pressure including subatmospheric, atmospheric and super-atmospheric pressures.

With reference now to FIG. 1, shown is an illustrative overall citrate ester production process in accordance with the invention. Sugar, nutrients and a citric acid-producing microorganism, are charged to a fermenter 1 wherein the fermentation is conducted. A citric acid fermentation broth from the fermentation, typically at a concentration of about 15 weight % citric acid, and including sugars and cations, is passed to clarifier 2 and clarified (filtered) to remove the cell mass. The clarified broth is then passed to cation remover 3 and treated to remove cations. For example, the cation remover 3 can be a cation exchange resin as discussed in the passages above. The cation-depleted broth is then passed to a concentration unit 4 and concentrated, e.g. by an evaporative process. For example, concentration 4 can conveniently be a falling film evaporator. The resulting concentrated broth is then charged to a reactor 5 for the esterification, along with the alcohol, catalyst, and any inert organic solvent to be used. The esterification reaction is desirably agitated, and can be conducted in a batch mode or a continuous mode. Preferably, the esterification is conducted in a continuous fashion with continuous addition of citric acid source, alcohol, catalyst, and optional solvent to the reactor 5, and continuous removal of the aqueous/organic phase reacted mixture from the reactor 5. In this regard, such a continuous reaction is conveniently conducted in a continuous stirred tank reactor (CSTR), a continuous tube reactor preferably adapted to stir or otherwise agitate the reaction mixture as it traverses the tube, or other similar equipment.

In such a continuous reaction, the average residence time of the reactants in reactor 5 is controlled so as to achieve the desired conversion to the citrate ester product, providing an aqueous phase and a separate organic phase containing the ester product. Residence time within the reactor 1 will depend upon several factors including the temperature of the reactor, the reactivity of the alcohol with the citric acid, the level of conversion desired, and other like factors which will be readily selected and controlled by the skilled artisan. Typical residence times within the reactor will however, be about 0.5 hours to about 10 hours, more often falling in the range of about 1 to 5 hours. The reacted mixture including aqueous and organic phases is then passed to separator 6, wherein the organic phase is separated from the aqueous phase. Separator 6 can be, for example, a conventional layer separation device such as a continuous decantor, or the like. The aqueous layer containing sugars can be passed to waste. The organic layer, containing the citrate ester product, can be further purified, for example by passage to a distillation column 7 for distillation to remove any remaining water, alcohol, and/or solvent, to provide a purified citrate ester. Prior to any such distillation, the citrate ester product, when relatively water-insoluble, can be also washed with an aqueous medium to further remove water-soluble impurities. In addition, the citrate ester composition can be treated to decolorize the same, e.g. by bleaching or other suitable means.

A wide variety of citrate esters can be prepared in accordance with the invention,s by reacting citric acid source with one or more alcohols typically having up to about 30 carbon atoms. In this regard, a single alcohol or a mixture of alcohols can be used to prepare esters in accordance with the invention. Typically, though, a single alcohol will be used. When a citrate triester is the desired product, it will be preferred to use at least 3 moles of alcohol per mole of citric acid in the esterification reaction.

As to preferred products, particularly advantageous citrate ester compositions prepared in accordance with the invention have the Formula (I)

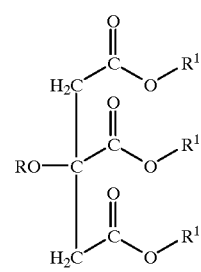

I wherein
R=H, R$^2$—CO— or Ph—R$^2_n$—CO— wherein R$^2$ is a C$_1$ to C$_{18}$ aliphatic group, n is 0 or 1, and Ph is a phenyl group;
each R$^1$, which can be the same or different from each other, is selected from H, a C$_1$ to C$_{18}$ aliphatic group or alicyclic group, or R$^2$(OR$^3$)$_m$— wherein R$^2$ is as defined above, R$^3$ is a C$_1$ to C$_8$ alkyl group, and m is an integer from 1 to 15; and
wherein up to about 40% of the groups R$^1$, taken together, are H (i.e. the carboxylic acid groups in the ester compositions are about 60% to about 100% esterified).

To prepare such preferred compositions, the citric acid source (e.g. from a clarified fermentation broth or otherwise partially-purified fermentation broth) is reacted with an alcohol of the formula R$^1$—OH, wherein R$^1$ is as defined above. Illustrative specific alcohols for use in the invention include methanol, ethanol, n-propanol, isopropanol, n-butanol, isobutanol, t-butanol, pentanol, hexanol, cyclohexanol,. heptanol, stearyl alcohol, oleyl alcohol, and the like, as well as alkoxy ether alcohols such as those having the formula $R^2(OR^3)_m$—OH wherein $R^2$ is a $C_1$ to $C_{18}$ alkyl group, more preferably a $C_1$ to $C_6$ alkyl group, $R^3$ is a $C_1$ to $C_8$ alkyl group, and m is an integer from 1 to 15, more preferably 1 to 5. Alkoxy ether alcohols suitable for use in the invention include monoalkyl ethers of alkanediols, for instance 2-ethoxyethanol, 2-propoxyethanol, 2-butoxyethanol, etc. as well as longer chain materials such as 2-(2-propoxyethoxy)ethanol, 2-(2-butoxyethoxy)ethanol, etc. Alkoxy ether alcohols utilizable in the invention are available via routes well known to the art and literature, and are also commercially available from Union Carbide Corp. of New York, N.Y. and Eastman Chemical Products of Kingsport, Tenn. Preferred groups $R^2(OR^3)$m— will contain about 30 carbons or less and more typically about 15 carbons or less.

In addition, the esterification is desirably conducted in the presence of an esterification catalyst. Suitable such catalysts are, generally known. In the present invention, preferred esterification catalysts are metal organic catalysts (e.g. organic titanates as disclosed in U.S. Pat. Nos. 4,711,922 and 4,824,893) as well as acid catalysts such as mineral acids (e.g. sulfuric acid or hydrochloric acid) and organic sulfonic acids.

Hydroxyl groups of the citric acid can also be converted to ester groups, generally by reaction with an acid halide or acid anhydride of an aliphatic, aromatic or combined aliphatic-aromatic carboxylic acid, typically having up to about 30 carbon atoms. Preferably, this reaction will be conducted after esterification of the carboxyl groups. Suitable starting materials for use in S this aspect of the invention include acid halides and anhydrides of acetic, propionic, butyric, pentanoic, hexanoic, heptanoic, nonanoic, etc., acids, on up to longer chain carboxylic acids such as oleic, linoleic and stearic acids. Benzoic acid halides or anhydrides are preferred aromatics for esterifying hydroxyl groups, although it will be understood that other similar aromatic carboxylic acid halides or anhydrides will be suitable and within the spirit and scope of the present invention. To prepare preferred compositions including esters of Formula (I) above, the acid halide or anhydride, if used, will have the formula $R^2$—CO—X or Ph(—$R^2$)$_n$—CO—X, or $R^2$—CO—O—CO—$R^2$ or Ph(—R )$_n$—CO-O-CO(—$R^2$)$_n$—Ph, wherein $R^2$ and n are as defined above and X is a halogen such as chlorine or bromine.

Preferred esterification reactions of the invention will generally be conducted at temperatures up to about 200° C., more typically up to about 150° C., e.g. about 50° C. to about 150° C., and can be driven to completion to form complete esters (e.g. wherein less than 5% of the groups $R^1$ in Formula 1 are H, preferably less than 2%) or in some aspects of the invention the reaction can be terminated when a desired, lower level of esterification has been achieved (e.g. wherein 5% to about 40% of the groups $R^1$ in Formula I are H), to form partial esters.

Citrate ester compositions prepared in accordance with the invention can be conventionally used as plasticizers to form modified polymer compositions, which also form a part of the present invention. For example, partial esters produced in accordance with the invention are more hydrophilic than their corresponding complete esters, the extent of which is dependent upon the level of esterification. This hydrophilic character can be capitalized upon when using the partial esters to physically modify compositions including degradable, relatively hydrophilic polymers such as cellulosic polymers (e.q. starch) and polyester polymers (e.g. poly(lactic acid) (see, e.g., U.S. Pat. No. 5,556,905). The full or essentially complete esters are particularly useful in the modification of PVC materials (see, e.g. U.S. Pat. Nos. 4,870,204; 4,789,700; 4,711,922; and 4,824,893).

The invention will now be more particularly described with reference to the following specific Examples. It will be understood that these Examples are illustrative and not limiting of the invention.

EXAMPLE 1

Four thousand grams of a mixture containing 600 grams of citric acid and 40 grams of α-D-glucose in 3360 grams of city water was concentrated at reduced pressure to a liquid temperature of 50° C. and a vapor temperature of 40° C. (90 mmhg) to give 857 grams of concentrate. The concentrate was combined with 500 mL of ethanol and 8.63 grams of p-toluenesulfonic acid and the mixture distilled at atmospheric pressure. During distillation, fresh ethanol was added at a rate of about 0.8 mL/minute to compensate for distillate being removed. Distillation was continued until the citric acid concentration in the reaction mixture reached 1.2%. The remaining ethanol was removed by further distillation at reduced pressure (liquid temperature of 110° C., 20 mmhg) to give 929 grams of concentrate containing triethyl citrate. The concentrate (101.5 grams) was distilled at reduced pressure (vapor temperature 168–186° C., 0.7 mmhg) to give 87.1 grams of C-2 ester having an acidity of 0.68% (as citric acid).

EXAMPLE 2

A fermentation broth (1225 grams) containing 47% citric acid and having been treated to remove cations, is combined with 732.6 grams of n-butanol, 10 grams of p-toluenesulfonic acid and 50 mL of toluene. The mixture is distilled at atmospheric pressure under Dean-Stark conditions to remove water. Care is taken to maintain the liquid temperature below 120° C. After five (5) hours or when 146 mL of water has been removed, a sample is removed from the reaction vessel and its citric acid content determined by titration. If the citric acid content is greater than 1.0%, additional toluene is added and distillation continued until the citric acid content of the reaction mixture is less than 1%. When the reaction is complete, excess toluene and n-butanol are removed at reduced pressure (liquid temperature 110° C., 25–30 mmhg). The tributyl citrate-containing concentrate is treated with aqueous soda ash (15–20%) and water to remove unreacted citric acid. Unwanted color can be removed by treating the concentrate with bleach or carbon.

EXAMPLE 3

The procedure of Example 2 is repeated, except the starting broth has also been treated to remove amino acids, to form a tributyl citrate product.

EXAMPLE 4

(A) Equilibration of the continuous stirred tank reactor: Three bed volumes (about 300 mL) of a solution containing 1016.4 g of water, 1016.4 g of citric acid, 1568.5 g of n-butanol, and 20.3 g of concentrated sulfuric acid were pumped with a peristaltic pump into a 500 mL, three-neck round bottom flask fitted with a mechanical stirrer and heated in an oil bath maintained at 150° C. After the reactor volume reached about 100 mL, reaction mixture was pumped from the reaction vessel at a rate to maintain a constant volume in the reactor. When the reactor had equilibrated, the temperature of the reactants had reached 127° C. All of the mixture removed during the equilibration was discarded.

(B) Esterification: A solution having the same volume and composition as the starting solution of part (A) above was pumped with a peristaltic pump into the equilibrated stirred reaction flask with continued heating at a rate of 0.77 mL/minute and reaction product removed at a rate to maintain a constant volume in the reactor. During the reaction, the temperature of the reactants remained at 127° C. and the reactants residence time within the reactor was 130 minutes. The reaction mixture (3618.2 g) removed from the reactor was allowed to cool and separate into layers and the lower layer (1076.7 g) removed,. The upper layer (2541.5 g) was washed with 500 mL of dilute sodium bicarbonate and three 500 mL portions of water. The organic layer was distilled to remove water and unreacted n-butanol and the concentrate analyzed by gas chromatography. The reaction was 94.1% complete after one pass through the CSTR and the resulting tributyl citrate 99.0% pure.

A solution containing 1016.4 g of water, 1016.4 g of citric acid, 1568.5 g of n-butanol, and 20.3 g of concentrated sulfuric acid was added to a glass round-bottom flask fitted with a heating mantle. The mixture was heated to 97° C. and refluxed for 72 hours to give a two-phase reaction mixture. The reaction mixture was worked up as described in Example 4. The reaction was 57.1% complete after the 72 hours.

The invention has been described above in detail, with specific reference to its preferred embodiments. It will be understood, however, that a variety of modifications and additions can be made to the procedures disclosed without departing from the spirit and scope of the invention. Such modifications and additions are desired to be protected. In addition, all publications cited herein are indicative of the level of skill in the relevant art, and are each hereby incorporated by reference each in their entirety as if individually incorporated by reference and fully set forth.

What is claimed is:

1. A process for preparing a citrate ester, comprising:
   providing a citric acid-containing broth from a citric acid-producing fermentation, the broth having been treated to remove cationic impurities; and
   reacting said citric acid-containing broth with one or more alcohols to esterify the citric acid.

2. A process for preparing a citrate ester, comprising:
   providing a citric acid-containing broth from a citric acid-producing fermentation, the broth having been treated to remove cationic impurities, the broth containing about 1% to about 20% by weight of sugar(s); and
   reacting said citric acid-containing broth with one or more alcohols to esterify the citric acid and form said citrate ester.

3. A process for preparing a citrate -ester, comprising:
   (i) combining an alcohol and an aqueous citric acid source containing water-soluble impurities to provide a reaction medium having an aqueous phase;
   (ii) reacting the reaction medium to form a citrate ester, said citrate ester passing to an organic phase separate from said aqueous phase, said aqueous phase retaining the water-soluble impurities; and
   (iii) separating the organic phase, containing the citrate ester, from the aqueous phase.

4. A continuous process for preparing a citrate ester, comprising:
   (i) continuously feeding an alcohol, aqueous citric acid, and an esterification catalyst to a reactor to provide a reaction medium having an aqueous phase;
   (ii) continuously reacting the reaction medium to provide a reacted mixture including a citrate ester, said citrate ester passing to an organic phase separate from said aqueous phase; and
   (iii) continuously withdrawing the reacted mixture from the reactor.

5. The process of claim 1, wherein the citrate ester has the formula

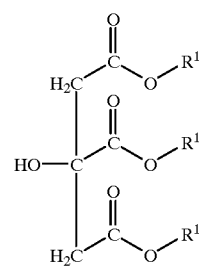

I wherein each $R^1$, which can be the same or different from each other, is selected from H, a $C_1$ to $C_{18}$ aliphatic group or alicyclic group, or $R^2(OR^3)_m$— wherein $R^2$ is a $C_1$, to $C_{18}$ aliphatic group, $R^3$ is a $C_1$ to $C_8$ alkyl group, and m is an integer from 1 to 15; and
   wherein up to about 40% of the groups $R^1$, taken together, are H.

6. The process of claim 5, wherein less than about 5% of the groups $R^1$ are H.

7. The process of claim 6, wherein each $R^1$, which can be the same as or different from each other, is selected from H and a $C_1$ to $C_{18}$ aliphatic group.

8. The process of claim 7, wherein each $R^1$, which can be the same as or different from each other, is selected from H and a $C_1$ to $C_6$ aliphatic group.

9. The process of claim 1, wherein said one or more alcohols includes n-butanol.

10. The process of claim 1, wherein said one or more alcohols includes ethanol.

11. The process of claim 1, wherein one alcohol is reacted with the citric acid, said one alcohol is n-butanol, and said citrate ester is tri-n-butyl citrate.

12. The process of claim 1, wherein one alcohol is reacted with the citric acid, said one alcohol is ethanol, and said citrate ester is triethyl citrate.

13. The process of claim 3, wherein said citrate ester is sufficiently insoluble in said aqueous phase to form said organic phase.

14. The process of claim 1, wherein said citrate ester is a citrate triester.

15. The process of claim 14, wherein said citrate ester is tributyl citrate.

16. The process of claim 1, wherein said citrate ester is water soluble, and said reaction medium also comprises a water-insoluble inert organic solvent.

17. A process for preparing tributyl citrate, comprising:
   reacting butanol with aqueous citric acid to form tributyl citrate, the reacting being conducted under conditions sufficient to provide a reacted medium including an aqueous phase and a separate organic phase containing the tributyl citrate; and separating the organic phase, containing the tributyl citrate, from the aqueous phase.

18. The process of claim 3, wherein the citrate ester has the formula

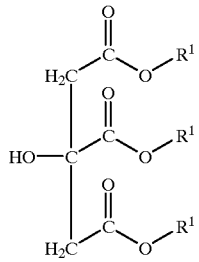

I wherein each $R^1$, which can be the same or different from each other, is selected from H, a $C_1$ to $C_{18}$ aliphatic group or alicyclic group, or $R^2(OR^3)_m$— wherein $R^2$ is a $C_1$ to $C_{18}$ aliphatic group, $R^3$ is a $C_1$ to $C_8$ alkyl group, and m is an integer from 1 to 15; and wherein up to about 40% of the groups $R^1$, taken together, are H.

19. The process of claim 18, wherein each $R^1$ which can be the same as or different from each other, is selected from H and a $C_1$ to $C_{18}$ aliphatic group.

20. The process of claim 3, wherein the water soluble impurities comprise about 1% to about 20% by weight sugar(s).

* * * * *

UNITED STATES PATENT AND TRADEMARK OFFICE
CERTIFICATE OF CORRECTION

PATENT NO. : 6,403,825 B1
DATED : June 11, 2002
INVENTOR(S) : Edward P. Frappier et al.

It is certified that error appears in the above-identified patent and that said Letters Patent is hereby corrected as shown below:

Column 3,
Line 40, please change "C8" to -- $C_8$ --.

Column 11,
Line 23, please insert the heading, -- EXAMPLE 5 --.
Line 58, please delete the hyphen before "ester,".

Signed and Sealed this

Twenty-sixth Day of November, 2002

Attest:

Attesting Officer

JAMES E. ROGAN
Director of the United States Patent and Trademark Office